United States Patent [19]

Booker

[11] Patent Number: 5,562,678

[45] Date of Patent: Oct. 8, 1996

[54] NEEDLE'S EYE SNARE

[75] Inventor: Robert Booker, Vandergrift, Pa.

[73] Assignee: Cook Pacemaker Corporation, Leechburg, Pa.

[21] Appl. No.: 458,827

[22] Filed: Jun. 2, 1995

[51] Int. Cl.$^6$ .............. A61B 17/22; A61B 17/28
[52] U.S. Cl. .......... 606/113; 606/108; 606/110; 606/106; 606/127; 606/205; 606/207
[58] Field of Search .................. 606/113, 108, 606/110, 79, 148, 1, 190, 191, 198, 127, 39, 46; 600/203, 206, 208, 209, 210, 217

[56] References Cited

U.S. PATENT DOCUMENTS

| | | | |
|---|---|---|---|
| 5,098,440 | 3/1992 | Hillstead | 606/113 |
| 5,108,406 | 4/1992 | Lee | 606/127 |
| 5,171,233 | 12/1992 | Amplatz et al. | 606/127 |
| 5,201,741 | 4/1993 | Dulebohn . | |
| 5,342,371 | 8/1994 | Welter et al. . | |

*Primary Examiner*—Robert A. Hafer
*Assistant Examiner*—Benjamin Koo
*Attorney, Agent, or Firm*—Richard J. Godlewski

[57] ABSTRACT

A reversible snare (10) for grasping and retrieving an article (15) such as a cardiac lead from within a human or veterinary patient (20) includes a sheath member (25) adapted for introduction into the patient (20), and a retractable closed loop (30) carried by the sheath member (25). The closed loop (30) is composed of a shape memory material and defines a hook (35) adapted to partly encircle the article (15). The snare further includes a threader (45) also carried by the sheath member (25), the threader (45) being reversibly extendable through the closed loop (30) (like a thread through a needle's eye) so that the hook (35) and threader (45) can fully encircle the article (15). Retraction of the closed loop (30) causes the hook (35) and threader (45) to close around the article (15) and permit its withdrawal into the sheath member (25). Independent retraction of the threader (45) allows the hook (35) to disengage from the article (15). The closed loop (30) and threader (45) are both preferably composed of nitinol wire, and the loop (30) possesses a nose (40) narrower than the inside diameter of the sheath member (25), in order to minimize deformation or fracture of the closed loop (30) during repeated extension and retraction. The sheath member (25) preferably includes conventional outer and inner femoral workstation sheaths (60 and 65), as well as an inner dilator sheath (55) carrying the closed loop (30) and threader (45). The snare (10) is particularly advantageous in that it can be repeatedly disengaged and reengaged with the cardiac lead or other article (15) without suffering any decrease in its utility or degradation of its components.

16 Claims, 4 Drawing Sheets

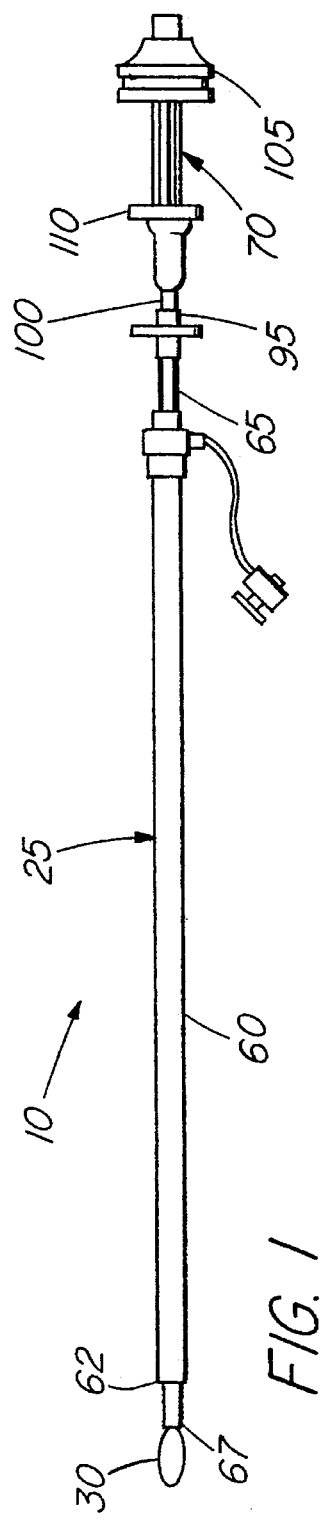
FIG. 1
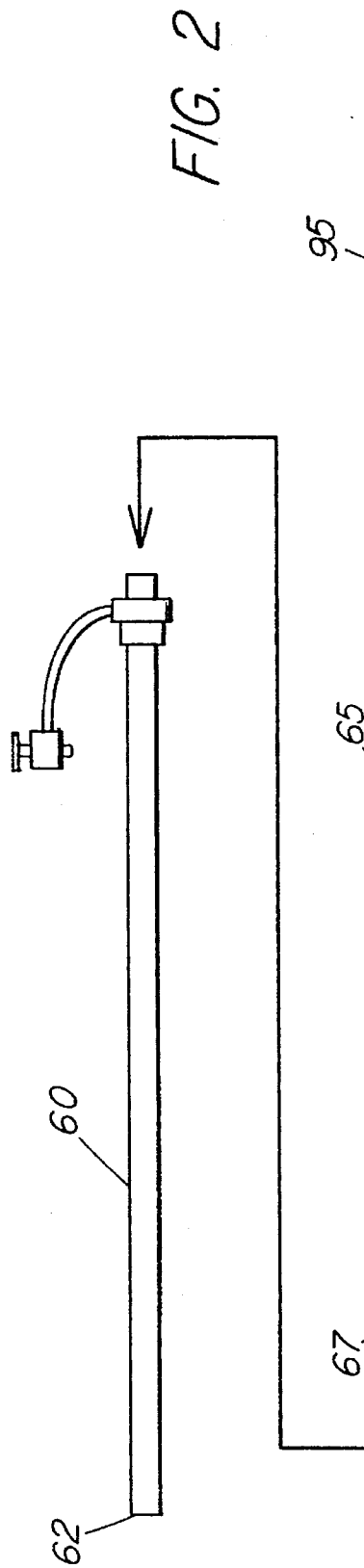
FIG. 2
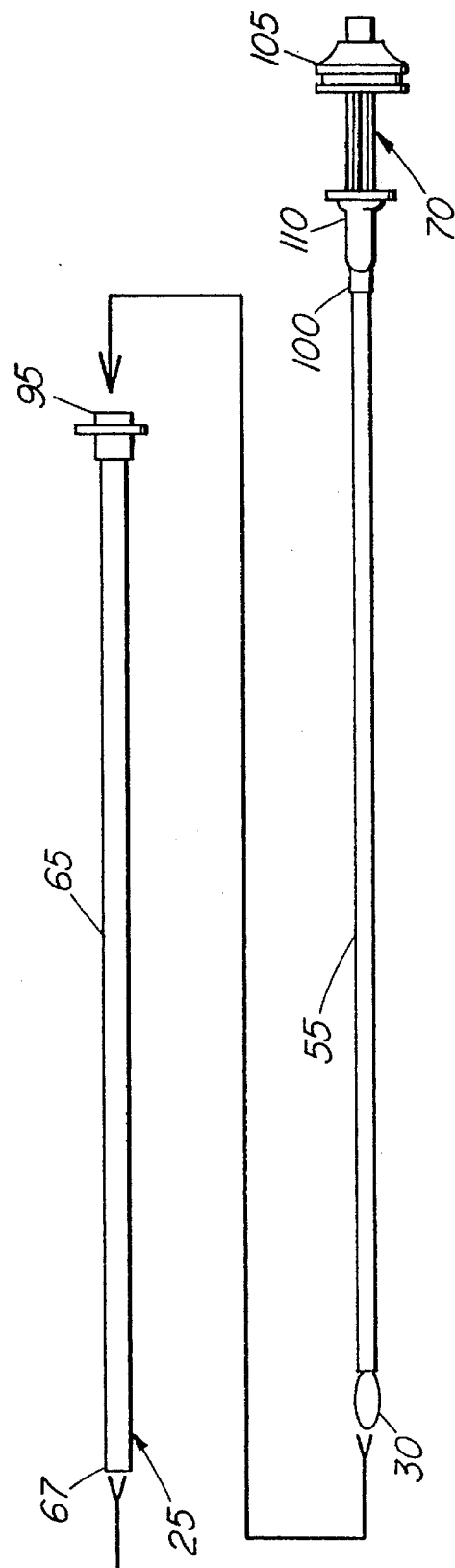

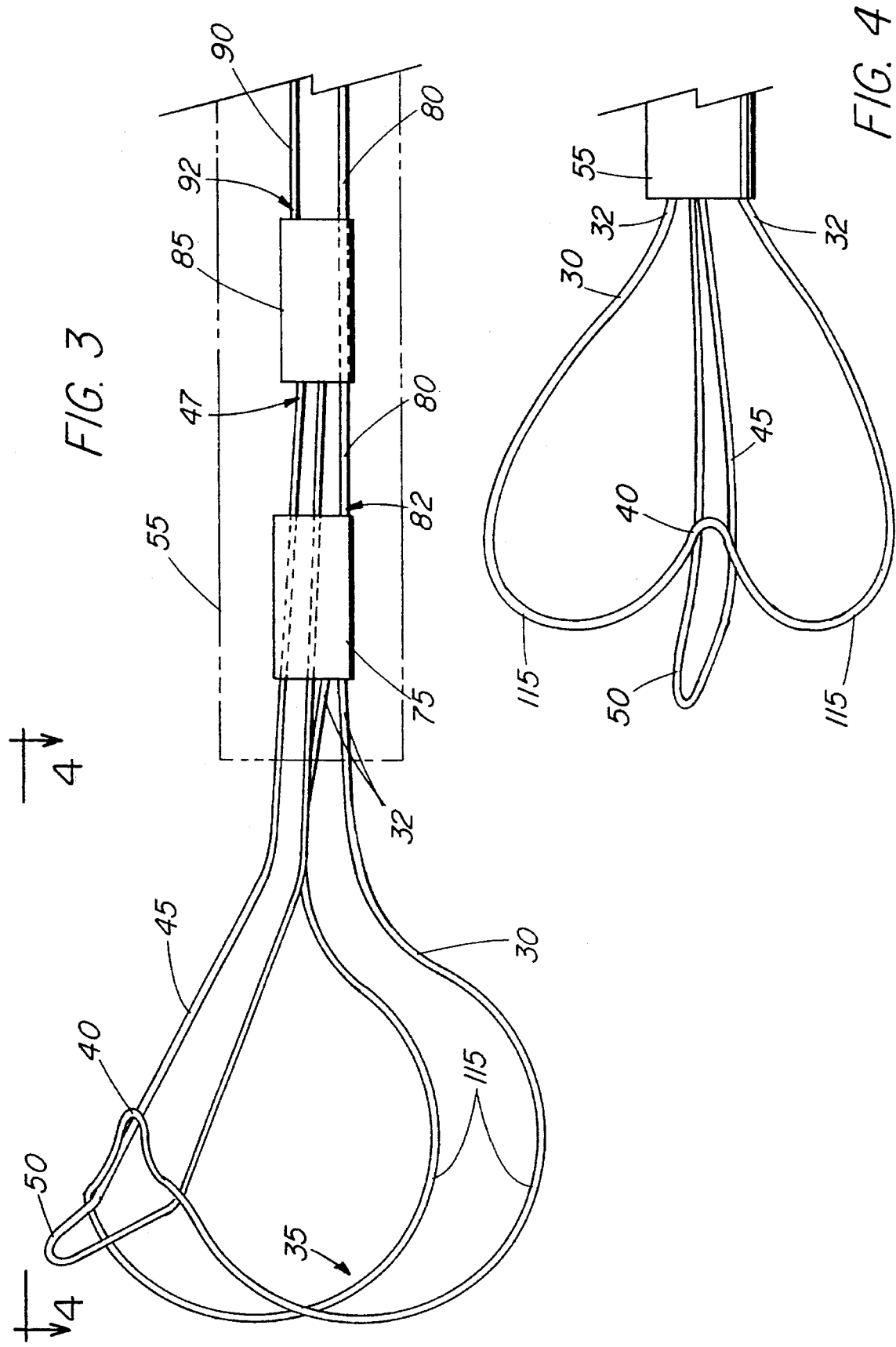

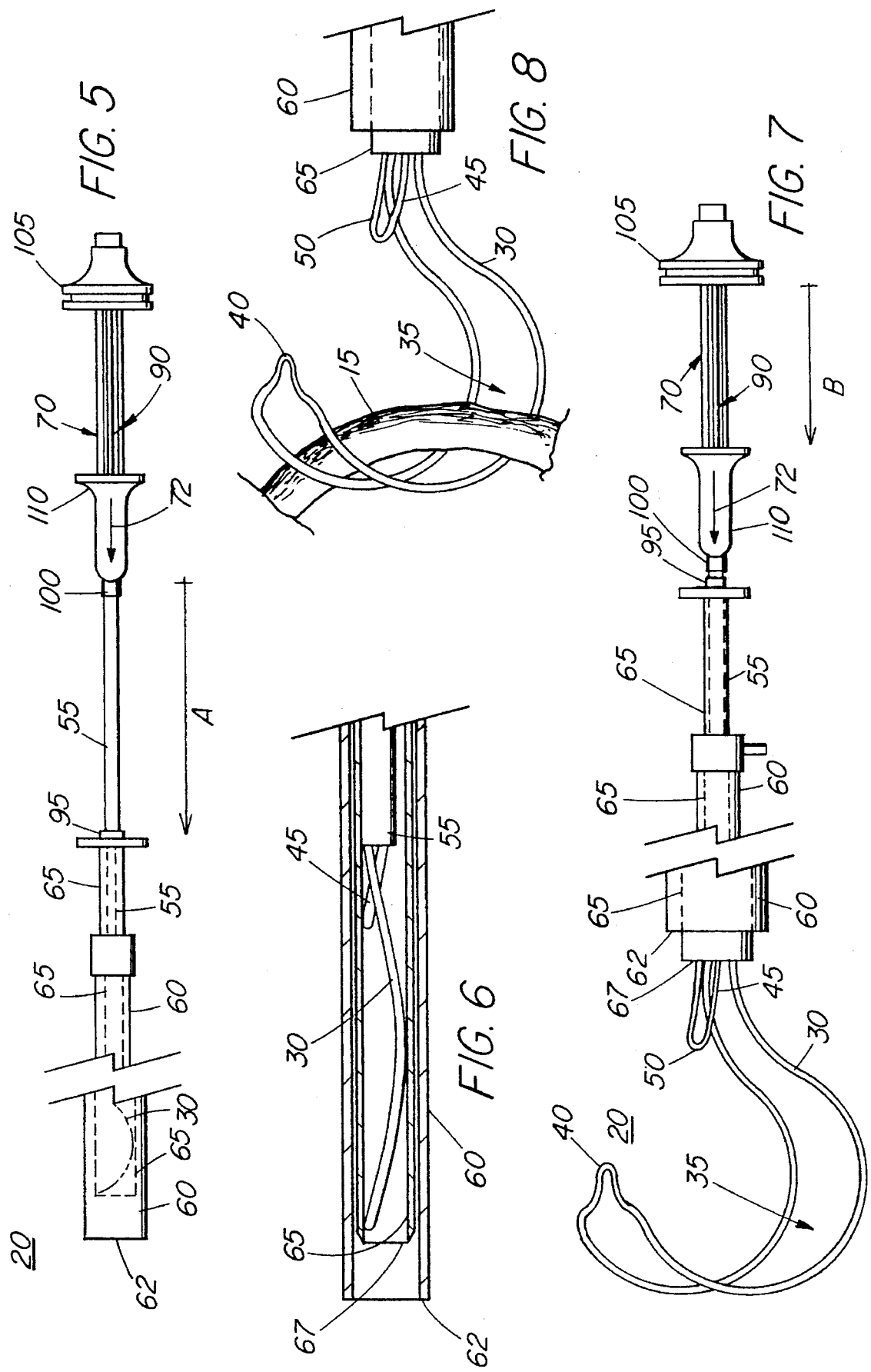

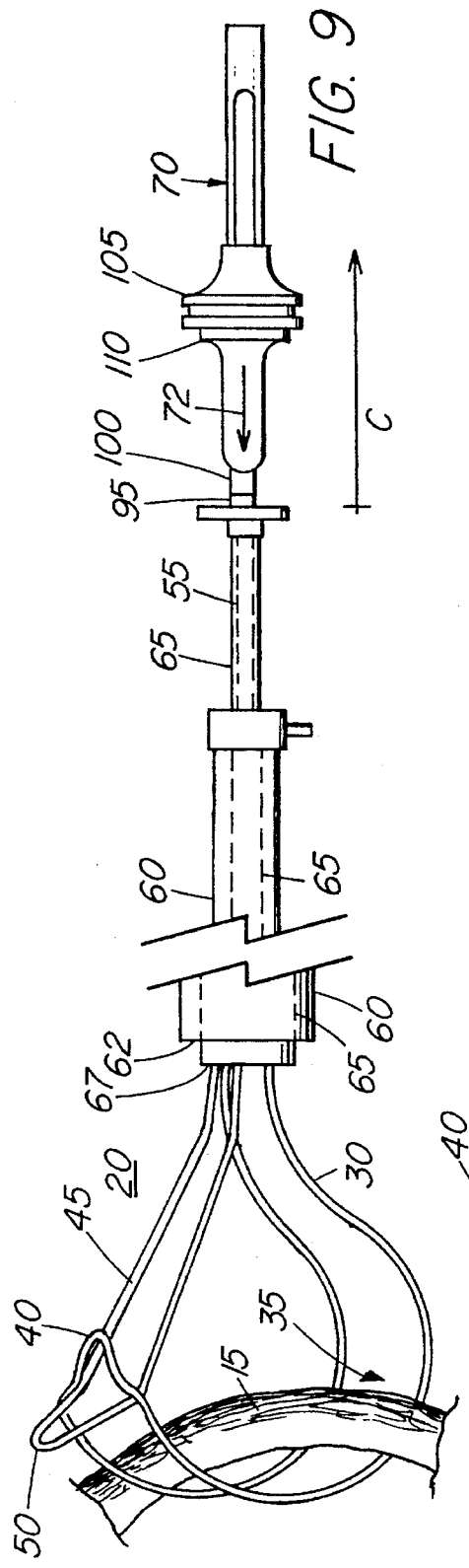
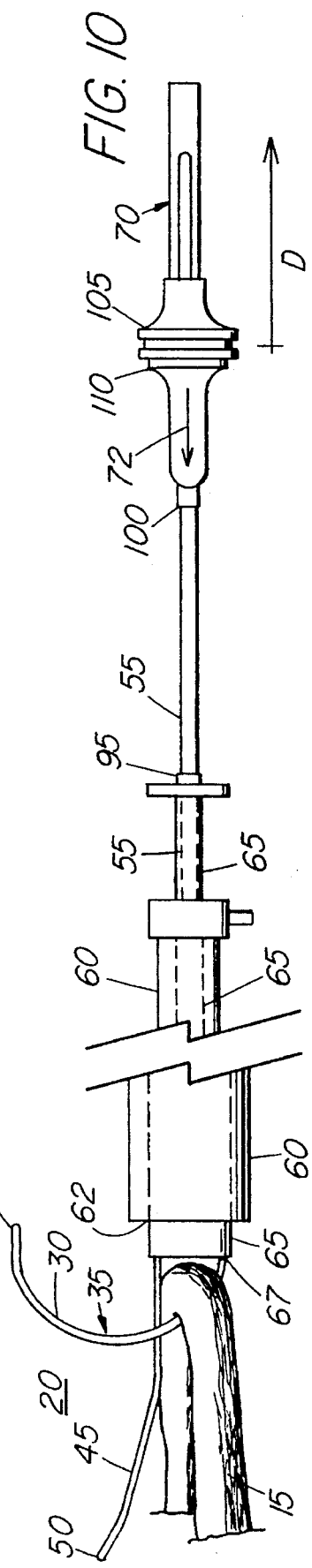
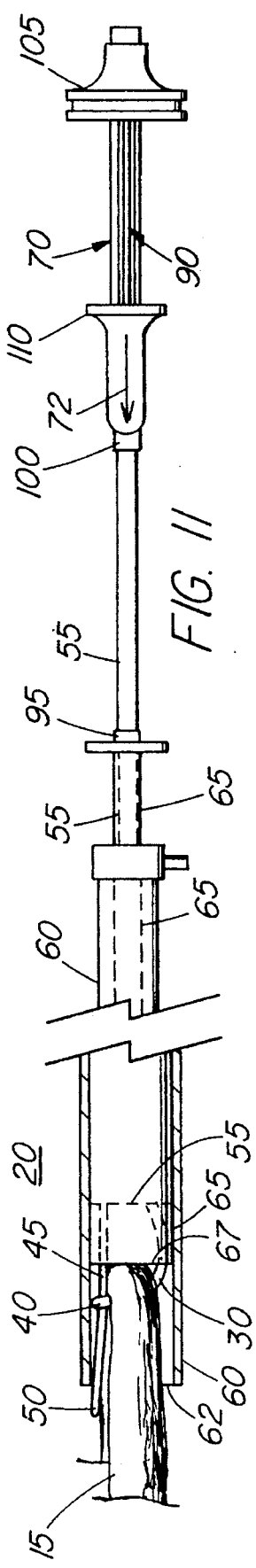

NEEDLE'S EYE SNARE

TECHNICAL FIELD

This invention relates generally to medical devices, and more particularly to devices for retrieving articles such as cardiac leads from human or veterinary patients.

BACKGROUND OF THE INVENTION

Medical devices such as catheters, wire guides, cardiac leads and the like have long been used to treat and improve the health of patients. Unfortunately, these devices occasionally break, fracture or fragment during use. Once broken or fragmented, a piece of a device can be released into the vascular system or elsewhere in the patient, even from such simple procedures as intravenous infusion or intravenous pressure monitoring. Any foreign body in the bloodstream has the potential to cause a number of clinical complications, including sepsis, perforation, thrombosis, arrhythmia, myocardial necrosis, and on occasion, even death. When such risk is encountered, it is urgent and vital to remove the foreign body from the patient, and a variety of approaches are known for such removal.

For example, open surgery is effective for removing a foreign body or article from the vascular system of a patient. Open surgery for this purpose is subject to numerous drawbacks, however. Open surgery is costly, is traumatic to the patient, requires long periods of patient healing and recovery, and entails its own risks of further complications. These risks are disproportionate to a patient who has only undergone a routine, noninvasive vascular access procedure.

Retrieval devices for removing a foreign body or article can be effective when employed in minimally invasive vascular access procedures. These procedures are typically performed with a visualization aid such as fluoroscopy, and several devices are known for this use.

For example, one known retrieval device has a distal hook. The distal hook is positioned centrally along the length of an elongated fragment or foreign body, and is pulled so as to drag the fragment through the vascular system and out of the patient's body. The use of such a device is subject to several drawbacks, however. The hook is unable to engage and pull a fragment or foreign body that is relatively short. Moreover, when the hook does engage the foreign body, the hook grasps it in a transverse orientation with respect to the axis of the retrieval device. As a result, the body extends from the hook at an angle, which makes it difficult to manipulate the hook and body through the tortuous vessels of the vascular system. The transversely extending foreign body can potentially stretch or catch on blood vessel walls and traumatize them. A further drawback of the hook type of device is that the elongated fragment or foreign body trails the hook in a doubled strand during travel through the tortuous vascular system. The fragment or body may cause significant drag or friction during removal, and since the hook lacks any structure to lock onto the fragment or body, the fragment or body may slide out of the hook, and again traumatize the blood vessel walls.

Another known type of retrieval device has a distal loop or snare which is positioned over a free end of the fragment or foreign body, and which is collapsed and tightened about it. One drawback to this type of device is that if the fragment or body is elongated, the snare grasps the fragment or body transversely with respect to the axis of the retrieval device. As with the hook type retrieval devices, the snare presents the fragment or foreign body transversely to the blood vessels through which it is pulled, potentially traumatizing the blood vessel walls. Further, the fragment or foreign body can become caught or wedged in the tortuous vessels and require surgical removal. Another problem with a distal loop or snare is that the wire making up the loop or snare can be easily kinked during introduction into the body, or during engagement with the fragment or body. Kinking often renders the snare ineffective, so that the snare must be replaced.

Yet another known retrieval device has a pair of distally positioned forceps jaws for grasping the fragment or foreign body anywhere along its length. One drawback in the use of jaw type devices is that the narrow, tortuous vessels of the vascular system offer limited space for the forceps jaws to open and close. Moreover, when the fragment or body is elongated, the jaws are typically used to grasp its central portion. As a result, the fragment or body has a transverse orientation with respect to the axis of the retrieval device, and encounters the same potential for traumatizing blood vessel walls disclosed above. Inadvertent release of the fragment or foreign body is also possible.

Several specific devices address some but not all of these problems. For example, the transverse positioning of the engaged fragment or foreign body is obviated in the helical snare disclosed in U.S. Pat. No. 5,342,371 (Welter et al., Aug. 30, 1994). That snare includes an elongated tubular member, and a filament wire exiting the member through inclined side ports, the distal portion of the wire being wrapped about the distal portion of the member. The wire forms a helical snare loop externally around the tubular member, which traps an elongated fragment or foreign body against the tubular member in an orientation parallel to it.

As additional examples, the kinking of a snare loop can be obviated by the use of a shape memory material for the snare, as in U.S. Pat. No. 5,201,741 (Dulebohn, Apr. 13, 1993) or U.S. Pat. No. 5,171,233 (Amplatz et al., Dec. 15, 1992). The best-understood shape memory material is the nickel-titanium alloy system known as "nitinol," which exhibits superelastic properties when maintained at a temperature above its transition temperature. The snares of the reference devices are composed of nitinol wire having a transition temperature below the operating temperature of the snare, for example, below body or room temperature. This allows the snares to be manipulated in relatively severe manners during introduction into the patient, but to recover their desired shapes (without kinking or other deformation) after such manipulation.

While neither reference addresses the problem of transverse orientation of the engaged fragment or foreign body, the device of Amplatz et al. does orient its nitinol loop at an angle with respect to an elongate proximal member on which it is carried. The loop of the Amplatz et al. device is provided with a small U-shaped arch at its distal tip to make it easier to insert the snare into the catheter which introduces it into the patient. The loop and distal tip preferably lie generally flat in a single plane, but the major axis of the loop may instead be curved. The specific utility of the curved loop does not appear to be expressly stated in the patent; however, since the purpose of the angle of the flat loop is to enhance the ability to slip the loop over an end of the foreign body to be retrieved, it can only be presumed that the purpose of curving the loop is also to facilitate slipping the loop over an end of the foreign body. There is no disclosure or suggestion that the curved loop of the Amplatz et al. device is intended to, or even can, function in the same way as the hook of the hook type retrieval devices mentioned above. Indeed, the superelasticity of the nitinol wire would appear to affirmatively prevent the curved loop from functioning like prior hooks. Accordingly, the Amplatz et al. device should still suffer some of the drawbacks associated with other snare type devices, most notably, that the snare loop must be placed over an end of the foreign body in order to engage it.

SUMMARY OF THE INVENTION

The foregoing problems are solved and a technical advance is achieved in an illustrative snare for reversibly grasping and retrieving from a patient an article such as a fragment, a foreign body or the like, especially an elongated article such as a cardiac lead, for example, a pacemaker or defibrillator lead. Applicant has discovered a way to engage such an article without having to slip a snare loop over an end of the article. This is particularly advantageous for articles having a long, unbroken length, such as intact cardiac leads.

More particularly, while a closed but hooked shape memory loop may not be able to laterally engage an article by itself, Applicant has discovered that extending a stop or threader through the loop permits the article to be fully and reversibly secured against the loop, upon partial retraction of the loop. To put it more simply, the stop or threader is extended through the closed loop just like a thread is passed through the eye of a needle. For this reason, the snare of the present invention can be conveniently referred to as a "needle's eye snare."

Once engaged in this manner, the encircled article can be manipulated as desired. Conveniently, the snare loop is delivered to the location of the article through one or more sheaths, and the snare loop and engaged article can be withdrawn from the patient through that same sheath, without moving the sheath. The sheath then shields the blood vessel walls or other body passages from any transversely oriented article. Should it become necessary to disengage the loop from the article, disengagement is achieved in an elegantly simple fashion, merely by extending the loop slightly and retracting the threader. The threader itself is preferably composed of a shape memory material, such as the same material as the closed loop, so that the engagement and disengagement of the snare with the article can be repeated as many times as desired. Current regulatory guidelines suggest that ten times is the minimum acceptable number, but when the closed loop is composed of a nitinol wire having a transition temperature below room temperature, the present invention is expected to be operable (engagement and disengagement) at least hundreds of times.

In a first aspect, then, the present invention is directed to a reversible snare for grasping and retrieving an article from within a human or veterinary patient, comprising a sheath member adapted for introduction into the patient; a retractable closed loop carried by the sheath member, composed of a shape memory material and defining a hook adapted to partly encircle the article; and a threader carried by the sheath member, the threader being reversibly extendable through the closed loop so that the hook and threader fully encircle the article, and retraction of the closed loop causes the hook and threader to close around the article. Preferably, the closed loop and the threader are slidably received in the sheath member, and are slidable within the sheath member independent of one another. The closed loop conveniently comprises a nose whose width is less than the inside diameter of the sheath member, as well as a pair of spread apart sides. Also preferably, at least the closed loop and conveniently both the closed loop and the threader are composed of nitinol wire or cable. The threader is preferably a generally straight, narrow wire loop having an angled end portion.

The sheath member can comprise only a single sheath, or two or more sheaths. Preferably, the sheath member comprises at least a dilator sheath carrying the closed loop and the threader. The closed loop is longitudinally fixed with respect to the dilator sheath, and the threader is longitudinally movable with respect to the dilator sheath. More preferably, the sheath member further comprises an outer workstation sheath, and an inner workstation sheath slidably received in the outer workstation sheath. The dilator sheath is slidably received in the inner workstation sheath. Optimally, the outer and inner workstation sheaths together comprise a femoral workstation. The sheath member can conveniently also comprise a handle and a slider carried by the handle, the closed loop being fixedly connected to the handle, and the threader fixedly connected to the slider.

In a second aspect, the present invention is directed to a specific combination of the various elements disclosed above.

The present invention is particularly advantageous in that it can be easily positioned on a cardiac lead or other article to be retrieved, and once in position can be easily and positively locked onto the lead or other article without fear of premature release, yet will release easily and reliably upon demand.

BRIEF DESCRIPTION OF THE DRAWING

A better understanding of the present invention will now be had upon reference to the following detailed description, when read in conjunction with the accompanying drawing, wherein like reference characters refer to like parts throughout the several views, and in which:

FIG. 1 is a perspective view of the preferred embodiment of the present invention;

FIG. 2 is an exploded perspective view of the preferred embodiment of the present invention;

FIG. 3 is a partial cross-sectional view of a portion of the preferred embodiment of the present invention;

FIG. 4 is a perspective view of a portion of the preferred embodiment of the present invention;

FIG. 5 is a perspective view of the preferred embodiment of the present invention during use;

FIG. 6 is a cross-sectional view of the left-hand portion of the embodiment shown in FIG. 5;

FIG. 7 is a perspective view similar to FIG. 5, also during use;

FIG. 8 is a perspective view of a portion of the preferred embodiment of the present invention, engaged with an article such as a cardiac lead; and FIGS. 9 through 11 are perspective views similar to FIGS. 5 and 7.

It is important to note that, for clarity of presentation, the left-hand portions of the views shown in FIGS. 5, 7 and 9 through 11 have been enlarged about three or four times with respect to the right-hand portions of those views.

DETAILED DESCRIPTION

With reference now to FIGS. 1 and 2, a reversible needle's eye snare 10 according to the present invention is thereshown and first comprises a sheath member 25 adapted for introduction into a patient 20, for example, into the vascular system of the patient 20 via the femoral artery. The sheath member 25 may of course be adapted for introduction elsewhere in the patient 20. The sheath member 25 can be a single sheath, or two or more sheaths, and as shown in FIGS. 1 and 2, preferably comprises three sheaths: an inner dilator sheath 55 slidably received in an inner workstation sheath 65, which in turn is slidably received in an outer workstation sheath 60. The inner and outer workstation sheaths 65 and 60 together comprise a conventional femoral workstation, and conveniently include connectors and the like (which need not be further identified) appropriate to such a workstation. The dilator sheath 55 and the inner and outer workstation sheaths 65 and 60 are composed of a suitable medical grade plastic, and preferably are radiopaque, so as to permit them to be located by a fluoroscope with respect to the article to be removed.

The snare 10 next comprises a retractable closed loop 30 carried by and slidably received in the sheath member 25. More particularly, the closed loop 30 is carried by and longitudinally fixed with respect to the dilator sheath 55. The closed loop 30 is composed of a shape memory material having a transition temperature below the body temperature of the patient, and preferably below room temperature. In this way, the closed loop 30 can be retracted into and extended from the sheath member 25 without kinking or alteration of the shape it possesses when extended from and unrestrained by the sheath member 25 (FIGS. 3 and 4). Most preferably, the closed loop 30 is composed of nitinol wire.

As more clearly shown in FIG. 3, the snare 10 of the present invention further comprises a threader 45 also carried by and slidably received in the sheath member 25. More particularly, the threader 45 is carried by the dilator sheath 55, but is longitudinally moveable with respect to it. In this manner, the closed loop 30 and the threader 45 are slidable within the sheath member 25 independent of one another. The threader 45 is conveniently but not necessarily composed of a shape memory material, preferably nitinol wire. The threader 45 is configured as a narrow wire loop and is generally straight; that is, when it is extended outward from the sheath member 25, it is capable of extending through the closed loop 30. Preferably, however, the threader 45 includes an angled distal end portion 50, to facilitate penetration of the closed loop 30. Further, as shown, the threader 45 may be bent slightly or otherwise shaped to optimize its engagement with the specific shape employed for the closed loop 30.

The sheath member 25 also comprises a handle 70 connected at its nose 100 to the dilator sheath 55. The closed loop 30 is fixedly connected, in a manner described below, to the handle 70. The sheath member 25 further comprises a slider 105 connected to but slidable along the handle 70, and the threader 45 is fixedly connected, in a manner described below, to the slider 105.

As disclosed in FIGS. 3 and 4, in its free state the closed loop 30 defines a curved hook 35, conveniently formed as a shape variously known as a shepherd's crook, a "C" or a "question mark." The closed loop 30 includes a narrowed nose 40 whose lateral width is less than the inside diameter of the sheath member 25, and in particular, less than the inside diameter of the dilator sheath 55. The narrowing of the nose 40 substantially reduces the chance of fracture of the loop 30 at the nose 40 from the stresses associated with repeated extension and retraction of the loop 30 out of and into the sheath member 25. This allows the target area, the interior of the closed loop 30, to remain intact through repeated usage, which is essential to the long-term utility of the snare 10.

The closed loop 30 also includes a pair of spread apart sides 115 on either side of the nose 40. Preferably, the closed loop 30 is formed from a single piece of wire, so that the nose 40 and sides 115 are continuously formed. The particularly preferred shapes and angular relations of the hook 35, nose 40 and sides 115 are shown in proportion in FIGS. 3 and 4.

The closed loop 30 is longitudinally fixed with respect to the dilator sheath 55, in particular, to the handle 70, by a loop positioning wire 80 affixed to the handle 70 at the flange 110. The loop positioning wire 80 is composed of a flexible but self-sustaining medical grade material, such as stainless steel stylet wire. The loop 30 is connected to the loop positioning wire 80 in any convenient fashion, such as by welding, braising, medical grade organic adhesive, or the like. Because the direct attachment of nitinol to stainless steel can be problematic, the loop 30 and positioning wire 80 are most conveniently connected mechanically by a loop crimping sheath 75 crimped about the ends 32 of the closed loop 30 and the distal end 82 of the positioning wire 80. The loop crimping sheath 75 is left partly hollow, however, to permit the passage therethrough of the threader 45.

The threader 45, in contrast, is longitudinally fixed with respect to the slider 105 carried on the handle 70, permitting movement independent of the movement of the closed loop 30. The threader 45 is connected to the slider 105 by a threader positioning wire 90. The threader positioning wire 90 is composed of a flexible but self-sustaining medical grade material, such as stainless steel stylet wire. The threader 45 is connected to the threader positioning wire 90 in any convenient fashion, again, such as by welding, braising, medical grade organic adhesive, or the like. The threader 45 and positioning wire 90 are most conveniently connected mechanically by a threader crimping sheath 85 crimped about the proximal end 47 of the threader 45 and the distal end 92 of the threader positioning wire 90. The threader crimping sheath 85 is left partly hollow, however, to permit the loop positioning wire 80 to pass freely through it.

Of course, the closed loop 30 and the threader 45 could themselves extend directly all of the way from the distal end 67 of the inner workstation sheath 65 to the handle 70. While this would lend great flexibility to the assembled snare 10, the superelasticity of the closed loop 30 and the threader 45 might make it difficult to readily advance them through the sheath member 25. Accordingly, it is preferred to use flexible but relatively stiffer elements (specifically, the disclosed positioning wires 80 and 90) to connect the closed loop 30 and the threader 45 to the handle 70 and the slider 105, respectively. Other connecting structures would be expected to work as well.

In any event, the threader 45 is reversibly extendable through the closed loop 30 by relative movement of the slider 105 and the handle 70. The hook 35 and threader 45 are thereby made capable of fully yet reversibly encircling the article 15 to be removed from the patient 20, and retraction of the closed loop 30 into the sheath member 25 causes the hook 35 and threader 45 to close around the article 15.

Use of the snare 10 to retrieve an article from a patient can now be easily understood. The most important point to remember during use of the snare 10 is that the extension and retraction of the closed loop 30 (the needle's eye) is controlled by relative movement of the sheaths 55, 60 and 65, while extension and retraction of the threader 45 is controlled by movement of the slider 105.

With reference first to FIG. 1, the relative positions of the sheaths 55, 60 and 65 are shown as the snare 10 is packaged prior to use. It should be clear that the snare 10 as shown is less than fully ready for use, because the closed loop 30 is exposed.

It is believed that packaging the snare 10 with the loop 30 fully extended has two specific advantages. First, it will make it easier for medical practitioners to learn how to use the snare 10, since they can see how the snare 10 will look inside the body when the loop 30 is extended and the hook 35 allowed to form. Second, it will make it easier for practitioners to visually and functionally evaluate whether the snare 10 is working properly, before introducing it into a patient. These advantages are only achieved when the transition temperature of the shape memory material of the loop 30 and threader 45 is below room temperature; while the snare 10 would still function properly in the patient's body with a transition temperature between room temperature and body temperature, the loop 30 and threader 45 would not be superelastic and therefore may not have their useful shapes when viewed by the practitioner before use.

The first step in using the snare 10 is thus to arrange the sheaths 55, 60 and 65 in the manner shown in FIG. 5, such that the slider 105 is in its most proximal position on the handle 70 (to the rights as seen in FIG. 5), and such that the nose 100 of the handle is separated from the proximal end 95 of the inner workstation sheath 65 sufficiently so that both the closed loop 30 and the threader 45 are fully contained within the inner workstation sheath 65. The outer workstation sheath 60 is then separated from the inner workstation sheath 65 and the dilator sheath 55, and introduced into the patient 20 (for example, through the femoral artery) until fluoroscopy shows that the distal end 62 of the outer workstation 60 is positioned near the article 15 (such as a cardiac lead) to be retrieved. The inner workstation sheath 65 and the dilator sheath 55 are then introduced into the outer workstation sheath 60, without movement relative to one another, until the distal end 67 of the inner workstation sheath 65 is positioned adjacent to the distal end 62 of the outer workstation sheath 60. Such a position is shown in cross-section in FIG. 6.

The closed loop 30 is then extended, and the hook 35 allowed to form, by moving the handle 70 in the direction of the arrow A shown in FIG. 5 until the nose 100 of the handle 70 abuts the proximal end 95 of the inner workstation sheath 65. This is the position shown in FIG. 7. With the hook 35 deployed, the snare 10 can be manipulated until the hook 35 engages and partly surrounds the article 15, e.g., a cardiac lead, to be retrieved. An arrow 72 on the side of the handle 70 indicates the position of the open side of the hook 35 to facilitate engagement; the engagement is shown in FIG. 8.

The article 15 is then completely encircled and engaged by moving the slider 105 distally, in the direction of arrow B in FIG. 7, until it abuts the flange 110 of the handle 70. This fully extends the threader 45 through the closed loop 30 and, as shown in FIG. 9, results in full encirclement of the article 15. Engagement of the snare 10 with the article 15 is then completed by moving the dilator sheath 55 outward (proximally) with respect to the inner workstation sheath 65, in the direction of arrow C of FIG. 9. Such relative movement of the inner workstation sheath 65 and the dilator sheath 55 retracts the threader 45 and closed loop 30, collapsing the hook 35 about the article 15 and securely but reversibly engaging it, and bringing the article 15 into abutment with the distal end 67 of the inner workstation sheath 65 (FIG. 10). The inner workstation sheath 65 is then moved outward (proximally) to further retract the engaged article 15 into the outer workstation sheath 60 itself, as shown in FIG. 11.

It should be noted that it is important that full travel of the threader 45 always be achieved every time it is extended or retracted. If not fully deployed, the threader 45 may be retracted into the inner workstation sheath 65 (and thereby disengaged from the closed loop 30) well before the article 15 abuts the distal end 67 of the inner workstation sheath 65, resulting in the inadvertent release of the article 15. It should also be apparent that full extension or deployment of the closed loop 30 (the needle's eye) requires that the nose 100 of the handle 70 butt directly against the proximal end 95 of the inner workstation sheath 65; if not, the target area (the interior of the loop 30) will not be fully formed, making it more difficult for the threader 45 to penetrate it.

Should it be necessary at any time to release the article 15 from the encircling hook 35 and threader 45, the slider 105 is simply moved proximally in the direction of arrow D in FIG. 10, and the snare pulled away from the article 15. Manipulation of the sheaths 55, 60 and 65 to retract the closed loop 30 for this purpose may be convenient but is probably not required, because the superelasticity of the loop 30 allows its disengagement from the article 15 with merely modest effort; the threader 45, now retracted, no longer prevents distal bending of the superelastic closed loop 30.

Although not preferred, it is possible to use the closed loop 30 to engage the cardiac lead or other article 15 without using the threader 45 at all. One way to do this is to use the loop 30 like the snare of other loop type devices, that is, to slip the loop 30 over an end of the article 15 and snug the loop 30 about it. Such use suffers the drawbacks common to loop type retrieval devices. Another way to use the snare 10 is to manipulate the closed loop 30 until the lead or other article 15 is positioned between the spread sides 115 of the loop 30; retraction of the loop 30 will pinch or trap the article 15 between the loop sides 115 and may in some cases be sufficient to secure the article 15 to the snare 10. This is the least reliable method of engagement, however, and should be considered only as a last resort. Quite simply, the snare 10 works best when the threader 45 is used in the manner disclosed.

It is therefore clear that the snare 10 of the present invention can be easily positioned on a cardiac lead or other article 15 to be retrieved from the body of a patient 20, and once in position, can be easily and positively locked onto the lead or other article 15 without fear of premature release. At the same time, the snare 10 can be released from the lead or other article 15 easily and reliably upon demand.

Of course, while the preferred embodiment of the snare 10 of the present invention is especially useful for retrieving a cardiac lead from a patient's vascular system, the snare 10 would also be useful for retrieving a variety of other articles from different locations in the patient's body, for example, from the gastrointestinal tract, the urinary tract, body ducts, and so on. Indeed, the snare 10 need not be introduced from a position outside the skin of the patient; rather, a convenient introduction site can be surgically exposed, and the snare 10 then introduced into the patient at that site.

Any undisclosed or incidental details of the construction or composition of the various elements of the disclosed embodiment of the present invention are not believed to be critical to the achievement of the advantages of the present invention, so long as the elements possess the strength or flexibility needed for them to perform as disclosed. The selection of these and other details of construction are believed to be well within the ability of one of even rudimentary skills in this area, in view of the present disclosure.

INDUSTRIAL APPLICABILITY

The present invention is useful in the performance of surgical procedures, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts.

What is claimed is:

1. A reversible snare (10) for grasping and retrieving an article (15) from within a human or veterinary patient (20), comprising:

a sheath member (25) adapted for introduction into the patient (20);

a retractable closed loop (30) carried by the sheath member (25), the closed loop (30) composed of a shape memory material, and the closed (30) loop defining a hook (35) adapted to partly encircle the article (15); and a threader (45) carried by the sheath member (25), the threader (45) being reversibly extendable through the closed loop (30) so that the hook (35) and threader (45) fully encircle the article (15), and retraction of the closed loop (30) causes the hook (35) and threader (45) to close around the article (15).

2. The snare (10) according to claim 1, wherein the closed loop (30) and the threader (45) are slidably received in the sheath member (25).

3. The snare (10) according to claim 2, wherein the closed loop (30) and the threader (45) are slidable within the sheath member (25) independent of one another.

4. The snare (10) according to claim 1, wherein the closed loop (30) comprises a nose (40) whose width is less than the inside diameter of the sheath member (25).

5. The snare (10) according to claim 1, wherein the closed loop (30) has a pair of sides (115), and the loop sides (115) are spread apart.

6. The snare (10) according to claim 1, wherein the threader (45) is composed of a shape memory material.

7. The snare (10) according to claim 1, wherein the threader (45) is generally straight.

8. The snare (10) according to claim 1, wherein the threader (45) is a narrow wire loop.

9. The snare (10) according to claim 1, wherein the threader (45) includes an angled end portion (50).

10. The snare (10) according to claim 1, wherein the sheath member (25) comprises a dilator sheath (55) carrying the closed loop (30) and the threader (45).

11. A reversible snare (10) for grasping and retrieving an article (15) from within a human or veterinary patient (20), comprising:

a sheath member (25) adapted for introduction into the patient (20);

a retractable closed loop (30) carried by the sheath member (25), the closed loop (30) composed of a shape memory material, and the closed (30) loop defining a hook (35) adapted to partly encircle the article (15);

a threader (45) carried by the sheath member (25), the threader (45) being reversibly extendable through the closed loop (30) so that the hook (35) and threader (45) fully encircle the article (15), and retraction of the closed loop (30) causes the hook (35) and threader (45) to close around the article (15);

wherein the sheath member (25) comprises a dilator sheath (55) carrying the closed loop (30) and the threader (45); and wherein the closed loop (30) is longitudinally fixed with respect to the dilator sheath (55), and the threader (45) is longitudinally movable with respect to the dilator sheath (55).

12. The snare (10) according to claim 11, wherein the sheath member (25) further comprises an outer workstation sheath (60), and an inner workstation sheath (65) slidably received in the outer workstation sheath (60); and wherein the dilator sheath (55) is slidably received in the inner workstation sheath (65).

13. The snare (10) according to claim 12, wherein the outer and inner workstation sheaths (60 and 65) together comprise a femoral workstation.

14. The snare (10) according to claim 1, wherein the closed loop (30) is composed of nitinol wire.

15. The snare (10) according to claim 1, wherein the sheath member (25) comprises a handle (70) and a slider (105) carried by the handle (70); and wherein the closed loop (30) is fixedly connected to the handle (70), and the threader (45) is fixedly connected to the slider (105).

16. A reversible snare (10) for grasping and retrieving a cardiac lead (15) from within a human or veterinary patient (20), comprising:

a sheath member (25) adapted for introduction into the patient (20), comprising an outer femoral workstation sheath (60), an inner femoral workstation sheath (65) slidably received in the outer workstation sheath (60), a dilator sheath (55) slidably received in the inner workstation sheath (60), a handle (70) affixed to the dilator sheath (55), and a slider (105) carried by the handle (70);

a closed loop (30) positioned within the dilator sheath (55) and fixedly connected to the handle (70), the closed loop (30) being composed of nitinol wire and defining a hook (35) adapted to partly encircle the cardiac lead (15), the closed loop (30) having a spread apart pair of sides (115) and a nose (40) whose width is less than the inside diameter of the dilator sheath (55), and the closed loop (30) being reversibly retractable upon relative movement of the dilator sheath (55) and the inner workstation sheath (65); and a threader (45) positioned within the dilator sheath (55) and fixedly connected to the slider (105), the threader (45) being composed of nitinol wire configured as a narrow loop and reversibly extendable through the closed loop (30) upon relative movement of the handle (70) and the slider (105); the threader (45) being generally straight but possessing an angled end portion (50) facilitating passage of the threader (45) into the closed loop (30); so that the hook (35) and threader (45) fully encircle the cardiac lead (15), and retraction of the closed loop (30) causes the hook (35) and threader (45) to close around the article (15).

* * * * *